United States Patent [19]

Nishikido et al.

[11] 4,297,503
[45] Oct. 27, 1981

[54] NOVEL BENZAMIDE DERIVATIVE AND METHOD OF PREPARING METOCLOPRAMIDE USING SAME

[75] Inventors: Joji Nishikido, Fuji; Nobuhiro Tamura, Chigasaki; Yohei Fukuoka, Kurashiki; Hiroyuki Yamane, Nobeoka, all of Japan

[73] Assignee: Asahi Kasei Kogyo Kabushiki Kaisha, Osaka, Japan

[21] Appl. No.: 190,994

[22] Filed: Sep. 26, 1980

Related U.S. Application Data

[62] Division of Ser. No. 58,809, Jul. 19, 1979, Pat. No. 4,250,110.

[30] Foreign Application Priority Data

Jul. 31, 1978 [JP] Japan .................... 53/92564

[51] Int. Cl.³ .......................... C07C 101/74
[52] U.S. Cl. ............................ 560/42
[58] Field of Search ................. 560/42

[56] References Cited

U.S. PATENT DOCUMENTS 3,177,252  4/1965  Thominet ................ 564/157
3,278,582  10/1966 Richter et al. ........... 560/42
3,725,417  4/1973  Holland ................. 560/42

FOREIGN PATENT DOCUMENTS 1146333  3/1969  United Kingdom .
1153796  5/1969  United Kingdom .

OTHER PUBLICATIONS

Wagner & Zook, Synthetic Organic Chem., John Wiley & Sons, Inc., N.Y., pp. 566–570, 1965.

*Primary Examiner*—G. T. Breitenstein
*Attorney, Agent, or Firm*—Finnegan, Henderson, Farabow, Garrett & Dunner

[57] ABSTRACT

2-Chloro-4-N-($\beta$-diethylaminoethyl)aminocarbonyl-5-methoxybenzamide of the formula,

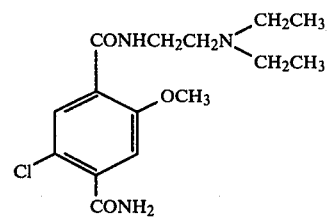

a process for their preparation and a process for preparing metoclopramide of the formula,

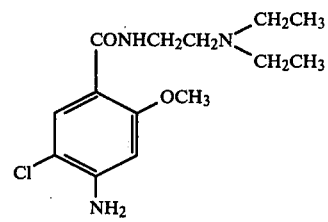

using the above described 2-chloro-4-N-($\beta$-diethylaminoethyl)aminocarbonyl-5-methoxybenzamide.

2 Claims, No Drawings

NOVEL BENZAMIDE DERIVATIVE AND METHOD OF PREPARING METOCLOPRAMIDE USING SAME

This is a division of application Ser. No. 058,809 July 19, 1979 now U.S. Pat. No. 4,250,110.

BACKGROUND OF THE INVENTION

1. Field of the Invention

This invention relates to a novel benzamide derivative and a method of preparing metoclopramide using the same.

2. Description of the Prior Art

Many methods are reported by preparing metoclopramide, i.e., N-(β-diethylaminoethyl)-2-methoxy-4-amino-5-chlorobenzamide useful as a antiemetic and an improving agent for digestion. Most of these methods use p-aminosalicylic acid as the starting material. More specifically, N-(β-diethylaminoethyl)-2-methoxy-4-amino-5-chlorobenzamide is prepared through each of the reaction steps including the methylation of the hydroxyl group at the 2-position of the benzene ring of the starting material, the chlorination at the 5-position of the benzene ring and the amidation of the carbonyl group with N,N-diethylethylenediamine.

One representative example of these conventional method is as follows;

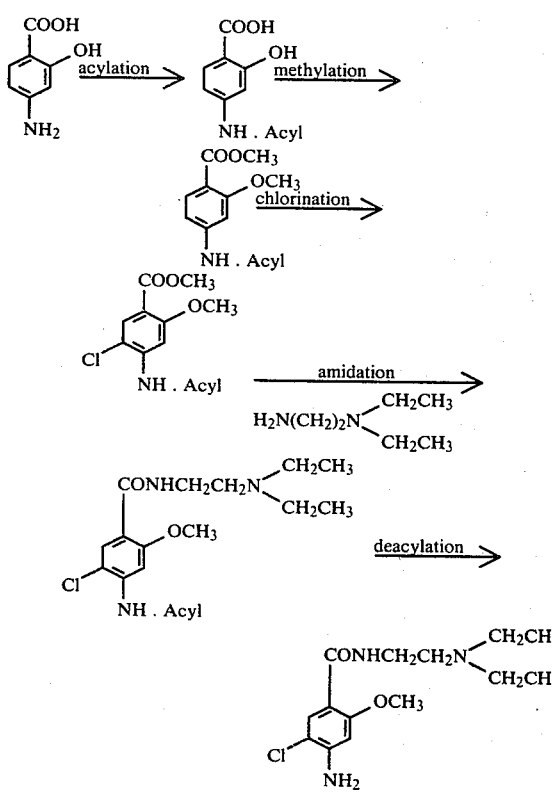

However, these conventional methods require complicated treatments in reaction, separation and purification of the above described steps and expensive reagents.

SUMMARY OF THE INVENTION

An object of this invention is to provide a novel benzamide derivative which can be used as a starting material for preparing metoclopramide and to provide a method of the production thereof.

Another object of this invention is to provide a method of preparing metoclopramide having high purity from the benzamide derivative.

Accordingly, the present invention in one embodiment provides 2-chloro-4-N-(β-diethylaminoethyl)aminocarbonyl-5-methoxybenzamide of the formula (I),

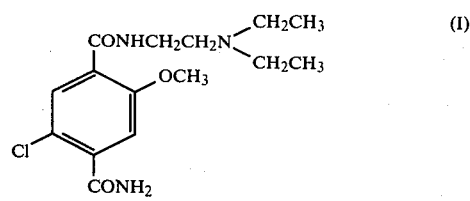

The present invention in another embodiment provides a method of preparing N-(β-diethylaminoethyl)-2-methoxy-4-amino-5-chlorobenzamide of the formula (V),

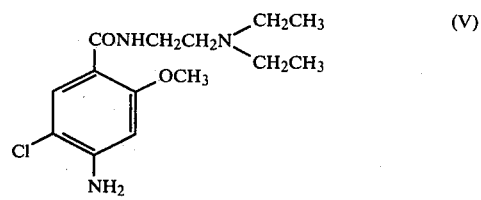

which comprises heating the compound of the formula (I) as described above.

In a further embodiment, the present invention provides 2-chloro-4-carboalkoxy-5-methoxybenzamide of the formula (II),

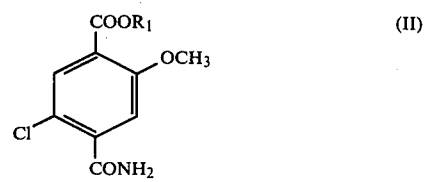

wherein $R_1$ is a $C_{1-7}$ alkyl group, a $C_{1-7}$ haloalkyl group or a phenyl group.

In an even further embodiment, the invention provides a method of preparing the compound of the formula (I) as described above which comprises reacting the compound of the formula (II) as described above with N,N-diethylethylenediamine.

In a still further embodiment, the invention provides a method of preparing the compound of the formula (I) as described above which comprises reacting 2-chloro-4-N-(β-diethylaminoethyl)aminocarbonyl-5-methoxybenzoic acid or its alkyl or aryl ester of the formula (IV),

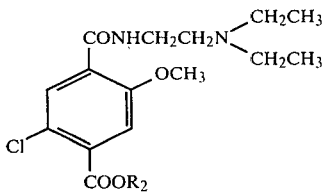

wherein $R_2$ is a hydrogen atom, a $C_{1-7}$ alkyl group, a $C_{1-7}$ haloalkyl group or phenyl group, with aqueous ammonia solution or ammonia gas.

DETAILED DESCRIPTION OF THE INVENTION

The method of preparing the compound of the formula (I) as described above and the method of preparing metoclopramide of the formula (V) as described above from the compound of the formula (I) will now be given.

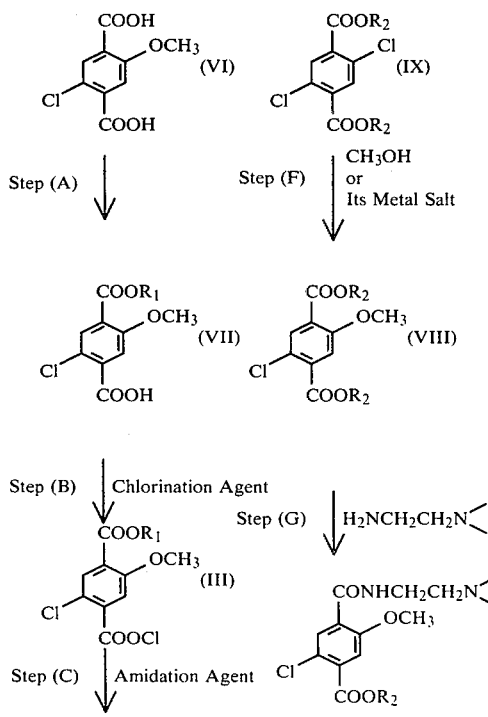

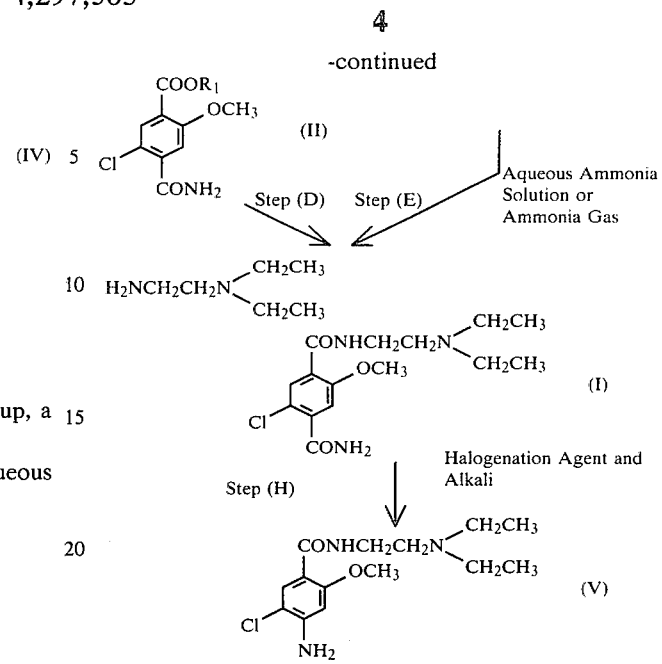

In the above described formulae (I) to (IX), $R_1$ is a $C_{1-7}$ alkyl group, a $C_{1-7}$ haloalkyl group or a phenyl group and $R_2$ is a hydrogen atom, a $C_{1-7}$ alkyl group, a $C_{1-7}$ haloalkyl group or a phenyl group. Suitable examples of the $C_{1-7}$ alkyl groups in the formulae (I) to (IX) include methyl group, ethyl group, n-propyl group, isopropyl group, n-butyl group, isobutyl group and n-pentyl group. Of these groups methyl group and ethyl group are preferred, and methyl group is more preferred. Suitable examples of the $C_{1-7}$ haloalkyl group in the formulae (I) to (IX) are $C_{1-5}$ haloalkyl groups such as monochloromethyl group, dichloromethyl group, monochloroethyl group, dichloroethyl group, monofluoromethyl group and monofluoroethyl group.

The reaction conditions in each of steps (A) to (H) will now be explained.

The compound of the formula (VII) is a novel compound. In step (A) the novel compound of the formula (VII) can be prepared by reacting 2-chloro-5-methoxyterephthalic acid of the formula (VI) with a $C_{1-7}$ alkyl alcohol, a $C_{1-7}$ haloalkyl alcohol or phenol in the presence of an acid catalyst including, for example, sulfuric acid, hydrochloric acid, p-toluenesulfonic acid and a Lewis acid such as boron trifluoride or aluminum chloride. The $C_{1-7}$ alkyl alcohol which can be employed in step (A) include, for example, methanol, ethanol, n-propanol, isopropanol, n-butanol, isobutanol and n-pentanol. The reaction temperature typically ranges from about $-20°$ C. to about $80°$ C. and preferably from about $0°$ C. to about $40°$ C. The reaction time typically ranges from about 10 minutes to about 5 hours, and preferably from about 30 minutes to about 2 hours.

Also, the novel compound of the formula (VII) can be obtained by reacting 2-chloro-5-methoxy-terephthalic acid of the formula (VI) with an esterification agent such as diazomethane or a $C_{1-7}$ alkyl halide such as methyl iodide or ethyl iodide in an organic solvent including, for example, ether, acetone, benzene and toluene. The reaction temperature typically ranges from about $-20°$ C. to about $150°$ C., and preferably from about $10°$ C. to about $60°$ C. and the reaction period of time ranges from about one hour to about 20 hours, and a preferred reaction period of time is about 5 hours. When the alkyl halide is employed, before the esterification of the compound of the formula (VI), the compound of the formula (VI) can be reacted with alkali such as potassium carbonate, sodium carbonate, potassium hydroxide and sodium hydroxide.

The reaction in step (B) for preparing the compound of the formula (III) can be conducted by reacting 2-chloro-4-carboalkoxy-5-methoxybenzoic acid of the formula (VII) with a chlorination agent without any reaction solvent or in the presence of a solvent such as benzene or acetone. Suitable chlorination agents which can be employed in the step (B) include thionyl chloride, phosphorus pentachloride, phosphorus trichloride and phosphorus oxychloride. The reaction temperature typically ranges from about 15° C. to about 100° C. and the reaction time typically ranges from about 10 minutes to about 5 hours, and preferably from about 30 minutes to about 2 hours.

In step (C) the compound of the formula (II), 2-chloro-4-carboalkoxy-5-methoxybenzamide, can be prepared by reacting 2-chloro-4-carboalkoxy-5-methoxybenzoic acid chloride of the formula (III) with an amidation agent. Suitable amidation agents which can be employed in the step (C) include ammonia gas, aqueous ammonia solution and ammonium carbonate. The reaction temperature typically ranges from about $-20°$ C. to about 30° C. and the reaction period of time typically ranges from about 10 minutes to about 5 hours, and preferably from about 30 minutes to about 2 hours.

The reaction of step (D) for preparing the novel compound of the formula (I) can be easily obtained by reacting 2-chloro-4-carboalkoxy-5-methoxybenzamide of the formula (II) with N,N-diethylethylenediamine without any reaction solvent or in the presence of a solvent. Suitable solvents which can be employed in the step (D) include water, methanol, dichloromethane, benzene, toluene and xylene. The reaction temperature typically ranges from about 20° C. to about 180° C. and a preferred reaction temperature ranges from about 50° C. to about 140° C. The reaction time typically ranges from about 0.5 to about 24 hours and preferably from about 2 to about 10 hours.

Further, in step (E) the novel compound of the formula (I) can be prepared by reacting the compound of the formula (IV) with aqueous ammonia solution or preferably ammonia gas in a sealed system for 1-10 hours. The reaction temperature typically ranges from about 100° C. to about 200° C., and preferably from about 130° C. to about 160° C. When aqueous ammonia solution is used, water is employed as a reaction medium. When ammonia gas is used, an inert solvent such as methanol, ethanol, tetrahydrofuran and dioxane can be employed as a reaction medium. If desired, the reaction in step (E) can be conducted in the presence of a small amount of catalyst including, for example, potassium hydroxide, sodium hydroxide and sodium methoxide. The amount of ammonia which can be employed in the step (E) typically ranges from about 0.8 to about 10 moles and preferably from about 1 to about 5 moles per mole of the compound of the formula (IV).

The compound of the formula (IV) can be obtained in steps (F) to (G).

The compound of the formula (IX) is known and can, for example, be easily obtained by reacting terephthalic acid with chlorine gas using iodine as a catalyst to form 2,5-dichloroterephthalic acid and, if desired, esterifying the 2,5-dichloroterephthalic acid with a $C_{1-7}$ alkyl alcohol such as methanol, ethanol, n-propanol, isopropanol, n-butanol, isobutanol and n-pentanol, a $C_{1-7}$ haloalkyl alcohol or phenol. Methanol is especially preferred.

The amount of iodine which can be employed as the catalyst typically ranges from about 1 to about 5% by mole based on the mole of terephthalic acid.

In step (F) the known compound of the formula (VIII) can be prepared by reacting the compound of the formula (IX) with methanol or a metal salt of methanol. When methanol is used, it is preferred to conduct the reaction in the presence of a catalyst including, for example, iodine, copper and copper iodide. Appropriate metal salts of methanol which can be employed in step (F) include alkali metal salts of methanol of which sodium methoxide is preferred. In this step methanol is employed as a reaction medium. The weight ratio of methanol to the compound of the formula (IX) which can be employed in step (F) typically ranges from about 2 to about 100. A preferred weight ratio ranges from about 5 to about 30. The reaction temperature typically ranges from about 100° C. to about 200° C., and preferably from about 130° C. to about 160° C. and the reaction period of time typically ranges from about 3 to about 6 hours. The reaction pressure which can be employed typically ranges from about 3 $Kg/cm^2$ to about 40 $kg/cm^2$.

The reaction of step (G) for preparing the compound of the formula (IV) can be conducted by reacting the compound of the formula (VIII) with N,N-diethylethylenediamine without any reaction solvent or in the presence of an inert reaction medium under heating to give the compound of the formula (IV) at high yields.

Suitable reaction media which can be employed in the step (G) include inert solvent such as water, methanol, dichloromethane, benzene, toluene, xylene, n-pentane, n-hexane, cyclohexane and any mixtures thereof.

The weight ratio of the reaction medium to the compound of the formula (VIII) which can be employed typically ranges from about 1 to about 100 and preferably from about 2 to about 50. The reaction temperature used typically ranges from about 20° C. to about 180° C. and a preferred reaction temperature ranges from about 50° C. to about 140° C. The reaction time typically ranges from about 1 to about 7 hours. The reaction pressure which can be employed typically ranges from atmospheric pressure to about 15 $Kg/cm^2$.

The amount of N,N-diethylethylenediamine which can be employed in the step (G) typically ranges from about 0.8 to about 3 moles and preferably from about 1.0 to about 1.5 moles per mole of the compound of the formula (VIII).

2-Chloro-4-N-($\beta$-diethylaminoethyl)aminocarbonyl-5-methoxybenzamide of the formula (I) is white crystals having 153°–154° C. of melting point, the same infrared absorption spectrum and NMR spectrum described in Examples below. The compound of the formula (I) is a novel compound and of use as the starting material for preparing metoclopramide of the formula (V).

Metoclopramide of the formula (V) can be obtained by subjecting the compound of the formula (I) to the same reaction condition as Hofmann rearrangement. Accordingly, the reaction of step (H) can be conducted by treating the compound of the formula (I) with a halogenation agent such as sodium hypobromite, potassium hypobromite, sodium hypochlorite, potassium hypochlorite, bromine or chlorine and an alkali. Suitable alkali which can be employed in the step (H) is sodium hydroxide or potassium hydroxide. The amount of the alkali typically ranges from about 1.0 to about 10 moles and preferably from about 2 to about 6 moles per mole of the compound of the formula (I). The amount of the halogenation agent typically ranges from about 1.0 to about 1.5 moles per mole of the compound of the formula (I).

For example, the reaction of step (H) can be conducted by dissolving the compound of the formula (I) in an alkali solution in which sodium hypobromite or potassium hypobromite has been dissolved and which was maintained at a temperature of about 5° C. with stirring and heating gradually at a temperature of 30° C. to 90° C. Then metoclopramide is separated from the alkali solution and can be easily obtained. Metoclopramide thus obtained can be highly purified by recrystallizing from methanol, ethanol or dioxane.

According to this invention, each of the above described steps (A) to (H) proceeds at high yields and high selectivities, and the products can be easily separated and purified, resulting in the desired products having high purity.

Thus, the method of this invention can give the desired products having higher purity at a lower cost than the conventional methods and is desirable from the industrial viewpoint.

The following Examples are given to illustrate the present invention more specifically. However, it should be understood that the invention is in no way limited by these Examples.

EXAMPLE 1

In 200 cc of absolute methanol were added 11.5 g of 2-chloro-5-methoxyterephthalic acid and dissolved therein. To the solution was added dropwise 7.7 cc of concentrated sulfuric acid over a period of 60 minutes under cooling. After the addition, the solution was agitated for 5 hours at a temperature of about 30° C.

The reaction solution was poured into 800 g of a mixture of ice and water and then extracted with 1000 cc of ether. The ether layer was further extracted with 500 cc of 5% aqueous ammonia solution. The extract was acidified with 5% hydrochloric acid to precipitate crystals. These crystals were separated by filtration to give 11.2 g of white crystals. These crystals were confirmed to be 2-chloro-4-carbomethoxy-5-methoxybenzoic acid from the following melting point, infrared absorption spectrum and elemental analysis values. The yield of crystals was 92%.

Melting Point: 152°–153° C.

Infrared Absorption Spectrum: 3000–2000 cm$^{-1}$ (—COOH), 1730 cm$^{-1}$ (—COOCH$_3$), 1700 cm$^{-1}$ (—CO— or —COOH)

Elemental Analysis Values for $C_{10}H_9ClO_5$: Calculated (%): C, 49.10; H, 3.68; Cl, 14.49: Found (%): C, 48.97; H, 3.68; Cl, 14.36.

2.45 g of the 2-chloro-4-carbomethoxy-5-methoxybenzoic acid were dissolved in 10 cc of thionyl chloride and the solution was refluxed under heating for 2 hours. After the reaction, excess thionyl chloride was removed from the solution to give 2.63 g of yellowish crystals. These crystals were confirmed to be 2-chloro-4-carbomethoxy-5-methoxybenzoic acid chloride from the following melting point, elemental analysis values, infrared absorption spectrum and NMR spectrum. The yield of crystals was 100%.

Melting Point: 84°–85° C.

Elemental Analysis Values for $C_{10}H_8O_4Cl_2$: Calculated (%): C, 45.63; H, 3.04; Cl, 27.0: Found (%): C, 45.17; H, 3.01; Cl, 26.5.

Infrared Absorption Spectrum (KBr disc): 3400 cm$^{-1}$, 1762 cm$^{-1}$, 1700 cm$^{-1}$, 1478 cm$^{-1}$, 1423 cm$^{-1}$, 1378 cm$^{-1}$, 1300 cm$^{-1}$, 1240 cm$^{-1}$.

NMR Spectrum (in CDCl$_3$, Tetramethyl Silane Internal Standard): 7.83 ppm 1H singlet (benzene ring), 7.57 ppm 1H singlet (benzene ring), 3.98 ppm 3H singlet (—COOCH$_3$), 3.92 ppm 3H singlet (—OCH$_3$).

2.63 g of the 2-chloro-4-carbomethoxy-5-methoxybenzoic acid chloride as obtained in the above described step were added to 20 cc of acetone, and further a large excess of aqueous ammonia solution was added thereto under cooling with ice to give 2.19 g of crystals. These crystals were confirmed to be 2-chloro-4-carbomethoxy-5-methoxybenzamide from the following melting point, elemental analysis values, infrared absorption spectrum and NMR spectrum. The yield of crystals was 90%.

Melting Point: 177°–178° C.

Elemental Analysis Values for $C_{10}H_{10}NO_4Cl$: Calculated (%): C, 49.28; H, 4.11; N, 5.75: Found (%): C, 49.03; H, 4.07; N, 5.69.

Infrared Absorption Spectrum (KBr disc): 3400 cm$^{-1}$, 1720 cm$^{-1}$, 1660 cm$^{-1}$, 1238 cm$^{-1}$.

NMR Spectrum (in DMSO, TMS Internal Standard): 8.00–7.77 ppm 2H broad (—CONH$_2$), 7.60 ppm 1H singlet (benzene ring), 7.30 ppm 1H singlet (benzene ring), 3.80 ppm 3H singlet (—COOCH$_3$), 3.75 ppm 3H singlet (—OCH$_3$).

2.10 g of the 2-chloro-4-carbomethoxy-5-methoxybenzamide were dissolved in 8.6 cc of N,N-diethylethylenediamine and refluxed under heating for 2 hours in a nitrogen atmosphere. After the reaction, excess N,N-diethylethylenediamine was removed from the solution under reduced pressure to give an oily substance. To the oily substance thus obtained were added 10 cc of water to precipitate white crystals. These crystals were separated by filtration, washed with water and then dried. The yield of crystals was 2.75 g (100%). These crystals were confirmed to be 2-chloro-4-N-($\beta$-diethylaminoethyl)aminocarbonyl-5-methoxybenzamide from the results of the following melting point, elemental analysis values, infrared absorption spectrum and NMR spectrum.

Melting Point: 153°–154° C.

Elemental Analysis Values for $C_{15}H_{22}N_3ClO_3$: Calculated (%): C, 54.96; H, 6.72; N, 12.82: Found (%): C, 54.63; H, 6.69; N, 12.76.

Infrared Absorption Spectrum (KBr disc): 3190 cm$^{-1}$–3420 cm$^{-1}$ (—CONH—, —CONH$_2$) 2810 cm$^{-1}$–2970 cm$^{-1}$ (—CH$_2$CH$_2$—, —CH$_2$CH$_3$).

NMR Spectrum (in CDCl$_3$, TMS Internal Standard): 8.56–8.10 ppm 1H broad (—CONH—), 8.00 ppm 1H singlet (benzene ring), 7.30 ppm 1H singlet (benzene ring), 7.23–6.60 ppm 2H broad (—CONH$_2$), 3.93 ppm 3H singlet (—OCH$_3$), 3.67–3.40 ppm 2H multiplet (—NHCH$_2$CH$_2$N<) 2.90–3.10 ppm 6H multiplet

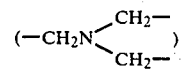

1.70–1.83 ppm 6H triplet

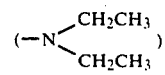

In a mixed solution of 1.65 g of bromine, 20 g of water, 5 g of ice and 1.83 g of sodium hydroxide were added little by little 2.75 g of the 2-chloro-4-N-(β-diethylaminoethyl)aminocarbonyl-5-methoxybenzamide as obtained in the above described step with agitation. The agitation was continued for one hour and the temperature was gradually raised to 50° C. and the reaction mixture solution was kept at 50° C. for one hour.

After the reaction, the reaction mixture solution was cooled at 5° C. for 5 hours to give light orange crystals. These crystals were separated by filtration and dissolved in methanol and left to stand at 20° C. for 10 hours to give 2.2 g of white needle-like crystals.

These crystals are identified as metoclopramide in comparison with the commercially available standard compound by ultraviolet absorption spectral analysis, infrared absorption spectral analysis and mass spectral analysis and melting point measurement.

Ultraviolet Absorption Spectrum: (Measured using 100% methanol solution. The maximum and minimum absorptions were in accord with those of the standard compound).

| Maximum Absorption (mμ) | Minimun Absorption (mμ) |
|---|---|
| 308 | 291 |
| 274 | 251 |
| 230 | |
| 213 | |

Infrared Absorption Spectrum: (Measured by the Kbr disc method. Each of the absorption were numbers was in accord with that of the standard compound.)
3200–3400 cm$^{-1}$ 3 Absorptions (—NH$_2$, —CONH—)
2800–2960 cm$^{-1}$ 5 Absorptions

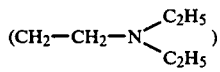

1645 cm$^{-1}$ 1 Absorption (—CON—), 1637 cm$^{-1}$ 1 Absorption (—CON—), 1595 cm$^{-1}$ 1 Absorption (benzene nucleus).

Mass Spectrum: (The molecular weight was 299 and each fragment as shown below was all in accord with that of the standard compound.) Fragment: 270, 227, 201, 184, 167, 100, 99, 86, . . .

Melting Point: 145°–146° C. (Standard Compound: 147° C.).

From the above described results the white needle-like crystals were confirmed to be metoclopramide.

EXAMPLE 2

23 g of 2-chloro-5-methoxyterephthalic acid were dissolved in 500 cc of absolute methanol. To the solution was added 500 cc of diazomethane ether solution containing 4.2 g of diazomethane at 20° C. After the solution was left to stand for one hour, ether was removed from the solution under reduced pressure. The residue was dissolved in 2,000 cc of ether and then treated by the same manner as in Example 1 to give 20.7 g of crystals of 2-chloro-4-carbomethoxy-5-methoxybenzoic acid.

20 g of the 2-chloro-4-carbomethoxy-5-methoxybenzoic acid were dissolved in 500 cc of benzene. To the solution were added 11.0 g of thionyl chloride and the solution was refluxed under heating for 2 hours. After completion of the reaction, the reaction solution was made alkaline by addition of ammonia gas under cooling and then benzene was removed from the reaction solution under reduced pressure. To the residue were added 1,000 cc of water and the mixture was stirred for 2 hours to give white crystals which were insoluble in water. The yield of crystals was 19.0 g (95%). These crystals were confirmed to be 2-chloro-4-carbomethoxy-5-methoxybenzamide by the same analytical methods as in Example 1.

4.9 g of the 2-chloro-4-carbomethoxy-5-methoxybenzamide was dissolved in 200 cc of xylene. To the solution were added dropwise 11.6 g of N,N-diethylethylenediamine dissolved in 10 cc of xylene under reflux over one hour and the reaction was further conducted at 137° C.–140° C. for 4 hours. After completion of the reaction, the reaction solution was treated in the same manner as in Example 1 to give 4.6 g of crystals. These crystals were confirmed to be 2-chloro-4-N-(β-diethylaminoethyl)-aminocarbonyl-5-methoxybenzamide by the same analytical method as in Example 1.

In a mixed solution of 33 g of 10% aqueous sodium hydroxide solution and 2.7 g of bromine were added little by little 4.6 g of the 2-chloro-4-N-(β-diethylaminoethyl)aminocarbonyl-5-methoxybenzamide as obtained in the above described step with vigorous agitation. The agitation was further continued for about 30 minutes and the temperature was gradually raised to 40° C. and the reaction mixture solution was kept at 40° C. for 30 minutes.

After the reaction, the reaction mixture solution was cooled at 5° C. for 5 hours to give light orange crystals. These crystals were separated by filtration and dissolved in methanol and left to stand for cooling at 20° C. for 6 hours to give 3.5 g of white needle-like crystals. These crystals were confirmed to be metoclopramide by the same identification method as in Example 1.

EXAMPLE 3

23 g of 2-chloro-5-methoxyterephthalic acid were dissolved in 500 cc of acetone. To the solution were added 9 g of potassium carbonate and further 250 cc of an acetone solution containing 31 g of ethyl iodide were added thereto and then the mixed solution was refluxed under heating for 3 hours. After completion of the reaction, the solvent was removed from the reaction solution under reduced pressure and the residue was dissolved in 1,000 cc of water. Then the solution was treated in the same manner as in Example 1 to give 23.5 g of crystals. These crystals were confirmed to be 2-chloro-4-carboethoxy-5-methoxybenzoic acid by the same analytical method as in Example 1. The elemental analysis values of the crystals were as follows: (for $C_{11}H_{11}ClO_5$)

Calculated (%): C, 51.08; H, 4.29; Cl, 13.71
Found (%): C, 50.06; H, 4.20; Cl, 13.25

4.9 g of 2-chloro-4-carboethoxy-5-methoxybenzoic acid were dissolved in 100 cc of acetone. To the solution was added 100 cc of benzene solution in which 4.5 g of phosphorus pentachloride had been dissolved in the mixed solution was refluxed under heating for 2 hours. After the reaction, to the reaction solution was added a large excess of saturated aqueous ammonium carbonate solution to give white crystals. These crystals were separated by filtration. The yield of crystals was 4.3 g. These crystals were confirmed to be 2-chloro-4-carboethoxy-5-methoxybenzamide by the same analytical methods as in Example 1.

In 1,000 cc of 50% aqueous methanol solution were added 4.3 g of 2-chloro-4-carboethoxy-5-methoxybenzamide and the solution was heated up to 65° C. Then to the solution were added 4.0 g of N,N-diethylethylenediamine and stirred at 65° C. for 10 hours. After completion of the reaction, the reaction solution was cooled to give 5.5 g of crystals. These crystals were confirmed to be 2-chloro-4-N-($\beta$-diethylaminoethyl)-aminocarbonyl-5-methoxybenzamide by the same analytical methods as in Example 1.

In a mixed solution of 3.2 g of bromine, 5.8 g of potassium hydroxide and 70 g of water were added 5.5 g of the 2-chloro-4-N-($\beta$-diethylaminoethyl)aminocarbonyl-5-methoxybenzamide as obtained in the above described step and the mixture was sufficiently stirred at 5° C. for 30 minutes and further stirred under heating at 35° C. for 3 hours. After completion of the reaction, the reaction solution was cooled at 5° C. for 10 hours to give crystals. These crystals were separated from the solution, dissolved in methanol and then left to stand for cooling at 20° C. for 5 hours to give 4.3 g of white needle-like crystals. These crystals were confirmed to be metoclopramide by the same identification methods as in Example 1.

EXAMPLE 4

In a 200 cc autoclave were charged 26 g of dimethyl 2,5-dichloroterephthalate, 6.5 g of sodium methoxide and 100 g of methanol, and the reaction was conducted at 160° C. for 6 hours. After the reaction, the reaction mixture solution was cooled to 20° C. and filtered. Part of methanol was distilled off from the filtrate and then the remaining solution was condensed and left to stand at 10° C. for 5 hours for cooling to precipitate white needle-like crystals. These crude crystals were separated and recrystallized from methanol to give 18.2 g of needle-like crystals of dimethyl 2-chloro-5-methoxyterephthalate having the following elemental analysis values.

Elemental Analysis Values: Calculated (%): C, 51.07; H, 4.26; O, 30.95: Found (%): C, 51.11; H, 4.20; O, 30.73.

In a 200 cc autoclave were placed 18 g of the dimethyl 2-chloro-5-methoxyterephthalate as obtained in the above described step, 8.3 g of N,N-diethylethylenediamine and 100 g of xylene and the reaction was conducted in a nitrogen atmosphere at 100° C. for 2 hours and further at 145° C. for 4 hours. After completion of the reaction, the xylene in the reaction mixture solution was distilled off under reduced pressure. The residue was added with methanol, dissolved therein under heating, added with hydrochloric acid and left to stand at 5° to 10° C. for 10 hours for cooling to precipitate white needle-like crystals. These crystals were separated by filtration and dried to give 22.2 g of methyl 2-chloro-4-N-($\beta$-diethylaminoethyl)aminocarbonyl-5-methoxy benzoate hydrochloride having the following infrared absorption spectrum and elemental analysis values.

Infrared Absorption Spectrum: 3350 cm$^{-1}$ and 1640 cm$^{-1}$ (—CONH—) 2980 cm$^{-1}$ and 2950 cm$^{-1}$ (—CH$_2$—, —CH$_2$CH$_3$) 2500–2730 cm$^{-1}$ (ammonium salt) 1730 cm$^{-1}$ (—COOCH$_3$).

Elemental Analysis Values: Calculated (%): C, 50.79; H, 6.08; N, 7.41; O, 16.93: Found (%): C, 50.68; H, 6.11; N, 7.37; O, 16.84.

In a 200 cc autoclave were placed 10 g of the methyl 2-chloro-4-N-($\beta$-diethylaminoethyl)aminocarbonyl-5-methoxybenzoate hydrochloride as obtained in the above described step, 2.0 g of ammonia gas and 100 g of methanol, and the reaction was conducted in a nitrogen atmosphere at 180° C. for 3 hours. After completion of the reaction, the reaction mixture solution was made weakly alkaline by addition of methanol solution of potassium hydroxide and the solution was filtered, and then unreacted ammonia and part of methanol were distilled off from the filtrate. The remaining filtrate was concentrated and left to stand for cooling to precipitate white crystals. These crystals were recrystallized from methanol to give 7.5 g of white needle-like crystals. These crystals were confirmed to be 2-chloro-4-N-($\beta$-diethylaminoethyl)aminocarbonyl-5-methoxybenzamide by the same analytical method as in Example 1. Elemental analysis values of the crystals were as follows:

Calculated (%): C, 55.05; H, 6.73; N, 12.84; O, 14.68
Found (%): C, 54.97; H, 6.66; N, 12.68; O, 14.77

3.8 g of potassium hydroxide were dissolved in 40 cc of water and to the solution were added 4.1 g of bromine under cooling with ice and the bromine was dissolved therein completely. To the solution were added and dissolved 7.5 g of 2-chloro-4-N-($\beta$-diethylaminoethyl)aminocarbonyl-5-methoxybenzamide and further 10 cc of water in which 5.4 g of potassium hydroxide had been dissolved were added thereto. The reaction was conducted under cooling with ice for one hour and the reaction temperature was gradually raised to 70° C. and the reaction was continued at 70° C. for 2 hours. After the reaction, the reaction mixture solution was left to stand for cooling at 5° C. for 10 hours to give 6.6 g of crystals. These crystals were confirmed as metoclopramide by the same identification methods as in Example 1.

EXAMPLE 5

In a 200 cc autoclave was charged 10 g of the methyl 2-chloro-4-N-($\beta$-diethylaminoethyl)aminocarbonyl-5-methoxybenzoate as obtained in the same manner as in Example 4, 3.3 g of 30% aqueous ammonia solution and 0.1 g of potassium hydroxide, and the reaction was conducted in a nitrogen atmosphere at 140° C. for 7 hours. After completion of the reaction, unreacted ammonia and part of methanol were distilled off from the reaction mixture solution and the remaining solution was concentrated and then left to stand for cooling to precipitate white crystals. These crystals were recrystallized from methanol to give 9.7 g of white needle-like crystals. These crystals were confirmed to be 2-chloro-4-N-($\beta$-diethylaminoethyl)aminocarbonyl-5-methoxybenzamide by the same analytical methods as in Example 1. The elemental analysis values of the crystals were as follows:

Calculated (%): C, 55.05; H, 6.73; N, 12.84; O, 14.66
Found (%): C, 55.10; H, 6.67; N, 12.85; O, 14.71

9.7 g of the 2-chloro-4-N-($\beta$-diethylaminoethyl)aminocarbonyl-5-methoxybenzamide as obtained in the above described step were treated in the same manner as in Example 1 to give 7.9 g of metoclopramide.

What is claimed is:
1. 2-Chloro-4-carboalkoxy-5-methoxybenzamide of the formula (II),

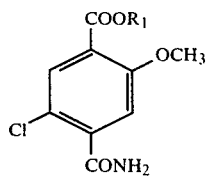

(II)

wherein $R_1$ is a $C_{1-7}$ alkyl group, a $C_{1-7}$ haloalkyl group or a phenyl group.

2. The compound of the formula (II) of claim 1, wherein the $C_{1-7}$ alkyl group is selected from the group consisting of methyl group, ethyl group, n-propyl group, isopropyl group, n-butyl group, isobutyl group and n-pentyl group.

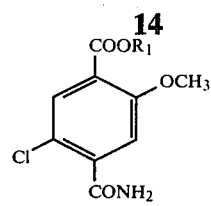

(II)

wherein $R_1$ is a $C_{1-7}$ alkyl group, a $C_{1-7}$ haloalkyl group or a phenyl group.

2. The compound of the formula (II) of claim 1, wherein the $C_{1-7}$ alkyl group is selected from the group consisting of methyl group, ethyl group, n-propyl group, isopropyl group, n-butyl group, isobutyl group and n-pentyl group.

UNITED STATES PATENT AND TRADEMARK OFFICE
CERTIFICATE OF CORRECTION

PATENT NO. : 4,297,503
DATED : October 27, 1981
INVENTOR(S) : JOJI NISHIKIDO ET AL.

It is certified that error appears in the above—identified patent and that said Letters Patent is hereby corrected as shown below:

Delete column 14 in its entirety

Signed and Sealed this

Second Day of February 1982

[SEAL]

*Attest:*

*Attesting Officer*

GERALD J. MOSSINGHOFF

*Commissioner of Patents and Trademarks*